United States Patent [19]

Mayer

[11] Patent Number: 5,597,536
[45] Date of Patent: *Jan. 28, 1997

[54] NEEDLELESS VACUUM CONTAINER PORT SYSTEM

[75] Inventor: Bruno Franz P. Mayer, Santa Ana, Calif.

[73] Assignee: Critical Device Corporation, Brea, Calif.

[*] Notice: The portion of the term of this patent subsequent to Jul. 22, 2014, has been disclaimed.

[21] Appl. No.: 608,529

[22] Filed: Feb. 28, 1996

Related U.S. Application Data

[63] Continuation of Ser. No. 279,496, Jul. 22, 1994.

[51] Int. Cl.$^6$ .............................. A61M 25/00; B01L 11/00
[52] U.S. Cl. ........................... 422/103; 422/99; 422/102; 422/104; 128/760; 128/764; 604/411; 604/412; 604/403
[58] Field of Search .............................. 422/99, 102, 103, 422/104; 128/760, 764; 604/403, 411, 412, 45

[56] References Cited

U.S. PATENT DOCUMENTS

| | | | |
|---|---|---|---|
| 3,977,555 | 8/1976 | Larson | 215/247 |
| 4,063,460 | 12/1977 | Svensson | 73/425.6 |
| 4,134,512 | 1/1979 | Nugent | 215/247 |
| 4,246,899 | 1/1981 | Loseff | 128/276 |
| 4,301,936 | 11/1981 | Percarpio | 215/247 |
| 4,338,764 | 7/1982 | Percarpio | 53/432 |
| 4,838,855 | 6/1989 | Lynn | 604/49 |
| 4,874,377 | 10/1989 | Newgard et al. | 604/167 |
| 5,064,416 | 11/1991 | Newgard et al. | 604/167 |
| 5,100,394 | 3/1992 | Dudar et al. | 604/283 |
| 5,122,129 | 6/1992 | Olson et al. | 604/905 |
| 5,135,489 | 8/1992 | Jepson et al. | 604/48 |
| 5,154,703 | 10/1992 | Bonaldo | 604/244 |
| 5,158,554 | 10/1992 | Jepson et al. | 604/283 |
| 5,171,234 | 12/1992 | Jepson et al. | 604/283 |
| 5,188,620 | 2/1993 | Jepson et al. | 604/283 |
| 5,273,533 | 12/1993 | Bonaldo | 604/83 |
| 5,286,453 | 2/1994 | Pope | 422/100 |
| 5,324,256 | 6/1994 | Lynn et al. | 604/49 |
| 5,360,012 | 11/1994 | Ebara et al. | 128/764 |
| 5,470,319 | 11/1995 | Mayer | 604/167 |

FOREIGN PATENT DOCUMENTS

| | | |
|---|---|---|
| 0544581 | 11/1992 | European Pat. Off. . |
| 3105437 | 10/1982 | Germany . |
| 3105437 | 6/1986 | Germany . |

OTHER PUBLICATIONS

Safe Tech Medical Products, Inc. "STAT–LINK", Universal Connector With Valve, 2 pp. (no publication date).

*Primary Examiner*—Jill Warden
*Assistant Examiner*—Harold Y. Pyon
*Attorney, Agent, or Firm*—Stetina Brunda & Buyan

[57] ABSTRACT

A needleless port system for depositing a sample of biological material into a vacuum container. The system comprises a generally dome-shaped or bell-shaped housing having an upper end and a bottom end, the latter being designed and configured to axially engage a vacuum container receivable therethrough. The system further includes at least one passageway, preferably disposed along a top portion thereof, for establishing fluid communication with a source of biological material. The system further preferably includes a hollow, generally spike-shaped member for depositing the biological sample into the vacuum container. Axially disposed within the housing and axially received about the generally spike-shaped member is a seal member designed and configured to penetrably and sealingly receive the distal tip of the spike member. The seal member is preferably designed and configured to selectively control the amount of biological material drawn into the vacuum container.

1 Claim, 2 Drawing Sheets

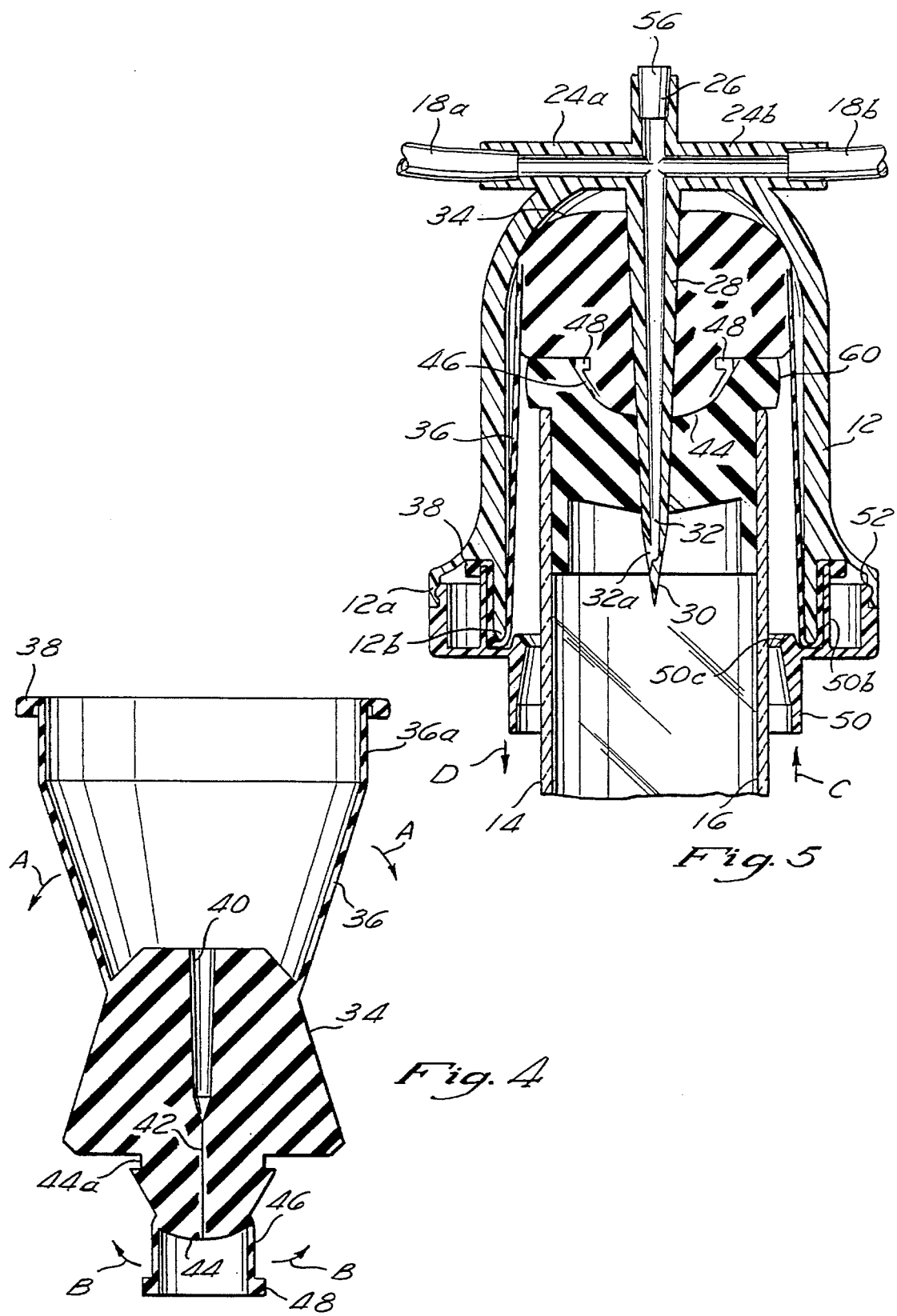

NEEDLELESS VACUUM CONTAINER PORT SYSTEM

This application is a continuation of application Ser. No. 08/279,496, filed Jul. 22, 1994.

FIELD OF THE INVENTION

The present invention relates to systems for collecting biological samples, and more particularly, to needleless port systems for depositing biological samples in a vacuum container.

BACKGROUND OF THE INVENTION

Containers for containing and storing biological samples, namely blood and other bodily fluids, are well-known to those skilled in the art. Most notable of such container devices are vacuum containers, i.e., containers formed to have a vacuum contained therein for facilitating the collection of blood and/or other bodily fluids. Generally, such vacuum containers or vacutainers are brought into fluid communication with the fluid sample to be collected, via a needle or catheter that is inserted through a septum formed on the container, wherein the vacuum disposed within the container provides means for drawing the fluid into the container. Additionally, such containers typically have amounts of an anti-coagulant, such as HEPARIN, present within the container to prevent coagulation of the sample once the sample has been collected.

While such vacuum containers offer great benefit as a means for containing and storing biological samples, current methods and systems for depositing biological samples into vacuum containers suffer from numerous drawbacks. Generally, such conventional vacuum containers utilize a dual needle system to establish fluid communication between the container and the source from which the biological sample is to be extracted. However, the use of needles to establish the necessary fluid communication is particularly disadvantageous due to the potential for a needle-stick experience to occur, which can thus increase the chances a healthcare worker could become infected with such blood-borne diseases as AIDS or Hepatitis-B.

In addition, conventional vacuum containers are generally accessed by means, such as needles, which may damage the septum formed on the vacuum container. As a result, these access or port systems may destroy the vacuum contained within the container or, alternatively, may cause the sample collected within the container to leak therefrom. Moreover, such port systems are generally ineffective in closing off the fluid communication established between the container and the source from which the biological sample is derived once a sufficient amount of sample has been collected. As such, excess biological material can spill about the container and cause contamination. Still further, these currently used systems generally may not be repeatedly used or, at best, may only be repeatedly used for a limited number of times due to the potential for such systems to become clogged or otherwise insufficiently allow a sample to be collected by the vacuum container.

Accordingly, it is apparent that there is a need in the art to provide a system through which biological samples may be collected in a vacuum container wherein the threat of a needle-stick experience is virtually eliminated. Additionally, there is a need in the art to provide a vacuum container port system through which a biological sample may be collected without the threat of the sample leaking from the system as well as a port system which may be repeatedly used and may be accessed by most conventional vacuum containers currently in use.

SUMMARY OF THE INVENTION

The present invention specifically addresses and alleviates the above-identified deficiencies in the art. More particularly, the present invention comprises a system which, when used in combination with a vacuum container, allows a sample of biological material to be deposited within the vacuum container without the use of needles. The invention comprises a generally dome or bell-shaped housing having an upper end and bottom end, the latter being designed and configured to axially engage a vacuum container receivable therethrough. The housing has at least one passageway disposed therein, preferably along a top portion thereof, which allows the sample of biological material to be received from a source and ultimately deposited within the vacuum container. The passageway includes a hollow, generally spike-shaped member that preferably depends from a top portion within the housing. The generally hollow, spike-shaped member is designed and oriented to pierce the septum of the vacuum container as the vacuum container is axially advanced within the housing.

Axially affixed within the housing is an elastic seal member designed and configured to selectively control the amount of biological material drawn into the vacuum container. More specifically, the seal member is oriented and configured to penetrably and sealingly receive the distal end of the generally spike-shaped member. Additionally, the seal member is biased to compress radially inward about the distal end of the generally spike-shaped member such that the passageway utilized to establish fluid communication between the biological source and the vacuum container is constantly closed off when the system is not in use. In a preferred embodiment, an annular member attachable to the bottom end of the housing is provided to provide means for affixing the seal member within the housing. Additionally, a dust cap, which is attachable to the annular member, is provided to prevent dust or other contaminating agents to enter into the housing when the system is not in use.

To operate the system, the vacuum container, with septum directed toward the bottom end of the housing, is axially advanced within the housing such that the septum abuts the seal member. By axially advancing the vacuum container within the housing, the septum formed on the container forces the seal member to axially retract about the spike member, thus allowing the spike member to pierce the septum and allow fluid communication to be established between the source of biological material and the vacuum container. Due to the vacuum formed within the vacuum container, biological material is drawn into the container. Once the desired amount of biological material is obtained, the vacuum container is axially withdrawn from the bottom end of the housing whereby the release of pressure against the seal member allows the seal member to axially advance about the distal end of the generally spike-shaped member, thus closing off fluid communication.

It is therefore an object of the present invention to provide a needleless vacuum container port system that effectively and efficiently allows a sample of biological material to be deposited within a vacuum container.

Another object of the present invention is to provide a needleless vacuum container port system that greatly reduces the potential for a needle-stick experience by the user of the same.

Another object of the present invention is to provide a needleless vacuum container port system that may be used with most conventional vacuum containers currently in use.

Another object of the present invention is to provide a needleless vacuum container port system that may be repeatedly used and effectively prevents biological material from leaking therefrom.

A still further object of the present invention is to provide a needleless vacuum container port system that is easy to use, inexpensive to manufacture, and is extremely durable.

BRIEF DESCRIPTION OF THE DRAWINGS

FIG. 4 is a cross-sectional view of the seal member of the needleless vacuum container port system; and FIG. 5 is a cross-sectional view of the needleless vacuum container port system having a vacuum container axially engaged therewith.

DETAILED DESCRIPTION OF THE PREFERRED EMBODIMENT

Figures 1, 2, 3:
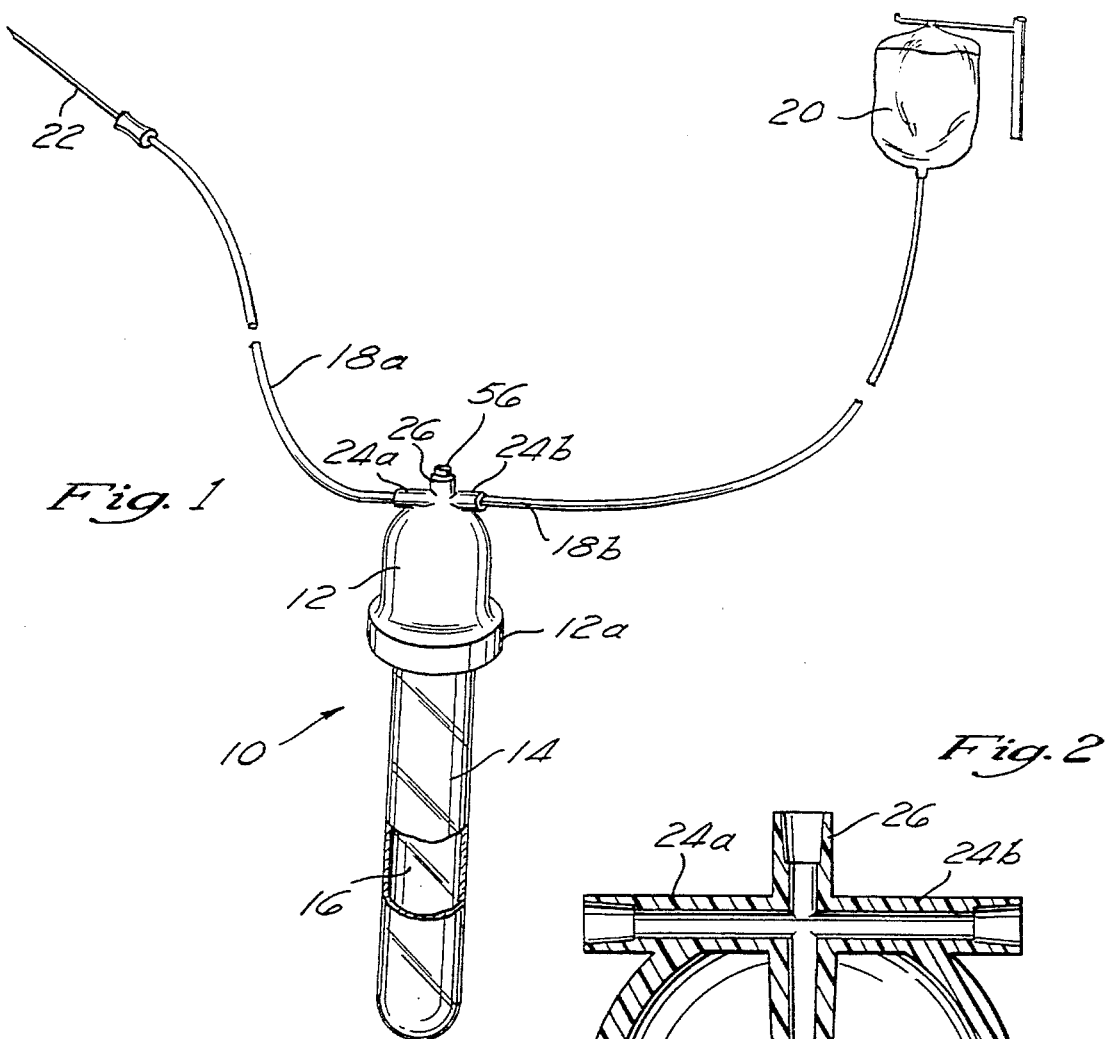
FIG. 1 is a perspective view of a needleless vacuum container port system according to a preferred embodiment of the present invention.
FIG. 2 is a cross-sectional view of the needleless vacuum container port system.
FIG. 3 is a perspective view of the distal end of the hollow, generally spike-shape member contained within the needleless container port system.

Referring now to the drawings, and more particularly to FIG. 1, there is shown a needleless vacuum container port system 10 according to a preferred embodiment of the present invention. The system 10 is specifically designed to be used in combination with a vacuum container 14 to allow a sample of biological material to be deposited within the container 14. Such vacuum containers 14 are well-known to those skilled in the art and are extensively utilized to obtain samples of biological fluids, most notably blood, so that the fluid may be analyzed in laboratory tests. Advantageously, by creating a vacuum within the interior of the container 16, such fluids are easily collected as the negative pressure draws such fluids into the container. In order to access the interior of the vacuum containers, a septum is usually provided with the container 14 to allow a sample to be deposited therein while preserving the vacuum and preventing contaminants from entering into the container 14.

With respect to the system 10 of the present invention, there is provided a generally bell-shaped or dome-shaped housing 12 having an upper end and lower end, the latter being designed and configured to axially engage a vacuum container 14 receivable therethrough. The housing further includes at least one passageway, formed by tubing ports 24a, 24b, and stopper port 26 preferably disposed along a top portion thereof, for establishing fluid communication between the vacuum container 14 and a source of biological material.

Typically, a needle 22, with catheter 18a extending therefrom, is inserted into the specimen from which the biological material is to be derived. Fluid communication thus becomes established between the specimen and the system 10 via needle 22, catheter 18a and tubing ports 24a, 24b, formed atop the housing 12. As will be recognized, such tubing ports 24a, 24b, as well as stopper port 26, define an inlet through which fluid communication may be established between the specimen and the vacuum container 14. Additionally, by including tubing ports 24a, 24b, the system 10 of the present invention may readily be hooked up to conventional I.V. systems via an intravenous line 18b, 20, between the patient or specimen and I.V. solution 20.

Referring now to FIG. 2, there is shown a cross-sectional view of the housing 12 of the needleless vacuum container port system 10 of the present invention. Preferably, depending from the top portion of the housing is a generally spike-shaped member 28 having a hollow passageway 32 disposed therein, the latter being in fluid communication with the passageway defined by tubing ports 24a, 24b and stopper port 26. The generally spike-shaped member 28, as more clearly seen in FIG. 3, includes a distal tip portion 30 that is preferably designed to have a sharpened pointed end. Passageway 32, which extends the length of spike member 28, extends through distal tip 30 to form three separate orifices 32a, 32b (32c not shown) thereon. Such multiple orifices 32a–c advantageously allows for more effective and efficient sample collection as such multiple orifices 32a–c increase the volume of fluid that may flow from passageway 32 to the interior of the vacuum container.

Referring again to FIG. 2, there is shown seal member 34 axially disposed within housing 12. The seal member 34 is oriented and adapted to penetrably and sealingly receive the distal tip 30 of spike member 20. The seal member 34 is further designed and configured to compress radially inward about the distal end 30 of spike member 28 such that fluid communication is closed off about distal tip portion 30. In particular, the distal tip portion 30 is embedded within aperture 40 of seal member 34 and is oriented towards spread seal 42, the latter providing a resealable closure that allows the system 10 to be repeatedly used. To maintain this inward radial compression about distal tip portion 30, seal member 34 is provided with a first inverted frusto-conical portion 36 which extends about the top portion of the seal member 34 and exerts, by virtue of its connection with housing 12, a downwardly biasing force. Additionally, first inverted frusto-conical portion 36 provides means for attaching the seal member 34 to the housing 12. As will be recognized, seal member 34, as well as all portions extending therefrom, is fabricated from elastic materials such that the seal member 34 may axially advance and retract about the spike member 28.

As further illustrated in FIG. 2, the seal member 34 additionally includes downwardly extending base portion 44 with a second inverted frusto-conical portion 46 extending upwardly thereabout. The second inverted frusto-conical portion 46 further has a second annular terminus 48 formed thereabout for engaging with an annular notch 44a, more clearly depicted in FIG. 4. The base portion 44 and second inverted frusto-conical portion 46 are specifically designed and configured to form an abutment surface upon which the septum of a vacuum container may be axially aligned. These additional elements, namely base portion 44 and second inverted frusto-conical portion 46, are likewise fabricated from elastic materials to allow these elements to axially retract and advance about the spike member 28.

To facilitate the attachment of the seal member 34 to the interior of the housing 12, there is further provided ring member 50 which is attachable to the bottom end of the housing 12. Ring member 50 preferably has three annular members 50a, 50b, 50c formed thereon that engage with the bottom end of the housing 12. More specifically, first annular member 50a engages with exterior annular portion 12a of housing 12 to provide means for attaching the ring member 50 to the housing 12, preferably by snap mounting. Second annular member 50b preferably sandwiches, along with interior annular flange 12b of the housing 12, a section of the first inverted frusto-conical portion 36 of the seal member 34. Preferably, the first inverted frusto-conical portion 36 of seal member 34 has a first annular terminus 38 formed thereabout to prevent the first inverted frusto-conical portion 36 from disengaging from second annular member 52b and interior flange 12b. Additionally, such first annular terminus 38 causes the seal member 34 to be constantly pushed downward and about the distal tip portion 30 such that no leakage may occur from the passageway 32 of the spike member 28. To keep the seal member 34 in position, annular member 50c is provided to abut against the seal member 34 and maintain the seal member 34 in the desired orientation. The needleless vacuum container port system 10 of the present invention further preferably includes a dust cap 54 which is attachable to the bottom end of ring member 50. Such dust cap 54 advantageously prohibits the introduction of any dust or contaminating agents which would otherwise taint the sample derived from the specimen.

Referring now to FIG. 4, there is shown the seal member 34 of the present invention formed to provide the specific functions disclosed herein. As discussed, the seal member 34 is fabricated from elastic materials well-known to those skilled in the art so that the seal member 34 may automatically form a resealable closure about the distal end 30 of spike member 28. Additionally, such elastic materials are essential to bias the seal member 34 axially downward to thus close off passageway 32. As shown, the seal member 34 has a generally hollow frusto-conical body portion with an upwardly extending first frusto-conical section 36 extending therefrom. The first frusto-conical portion 36 extends upwardly to form an annular rim 36a with first annular terminus 38 formed thereabout. To form the seal as shown in FIG. 2, the first hollow frusto-conical portion 36 is inverted about the frusto-conical portion of seal member 34 by inverting the first hollow frusto-conical portion 36 in the direction indicated by the letter A. Likewise, the base portion 44 has a second tubular portion 46 which inverts upwardly, as indicated by the letter B, to form the inverted frusto-conical configuration as shown in FIG. 2. Preferably, second annular terminus 48 is provided about the second tubular portion 46 which is preferably formed to extend upwardly and be received within annular notch 44a formed about base portion 44. Additionally formed on seal member 34 is an axially disposed aperture 40 along with spread seal 42 which, as will be recognized, cooperate to form an elastic valve element for penetrably and sealingly receiving the distal tip 30 of spike member 28.

Forming the seal member 34 to have the configuration as shown in FIG. 4, which may be done by a variety of methods known to those skilled in the art, advantageously allows the needleless vacuum container port system 10 to be repeatedly used while insuring proper close-off of distal tip 30. Additionally, such formation of the seal 34 according to the shape outlined above provides a simple mechanical mechanism by which such close-off is insured while also providing a port system that maintains constant protection about spike member 28, thus greatly reducing any potential for a needle-stick experience.

Referring to FIG. 5, there is shown the engagement between a vacuum container 14 and the device 10 of the present invention. Although not shown, dust cap 54 is initially removed from ring member 50 so that the interior of the housing 12 may be accessed by the vacuum container 14. As illustrated, the vacuum container 14, with septum 60, is axially advanced through ring member 50 and into the interior portion of the housing 12 as indicated by the letter C. The septum 60 of the vacuum container 14 axially abuts seal member 34 such that base portion 44 is axially disposed upon the septum 60. As those skilled in the art will appreciate, such base portion 44, along with second inverted frusto-conical portion 46, advantageously provide means for axially aligning the septum 60 with the seal member 34 such that the spike member 28 is axially positioned to be received within the vacuum container 14. As the vacuum container 14 and septum 60 are advanced in the direction indicated by the letter C, the septum 60 forces the seal member 34 to axially retract about spike member 28 such that distal tip portion 30 penetrates through spread seal 42 and eventually through the septum 60. As those skilled in the art will appreciate, the sharpened distal end 30 at no time becomes exposed to the outside environment during all stages of use of the device 10 of the present invention.

Once the distal tip portion 30 has penetrated through the septum 60 of the vacuum container 14, fluid communication thus becomes established between passageway 32, via apertures 32a–c (32b–c not shown), and the interior portion 16 of the vacuum container 14. Due to the vacuum present within the interior portion 16 of the vacuum container 14, fluid from the patient or specimen is drawn into the interior portion 16. The septum 60 and vacuum container 14 are maintained in the position shown in FIG. 5 for a duration sufficient to collect the desired amount of sample. Once the desired amount of sample has been collected, the vacuum container is axially retracted in the direction indicated by the letter D. By axially retracting the vacuum container 14, the seal member 34, due to the downwardly biasing force produced by stretched first frusto-conical portion 36, axially advances about the spike member and thus seals off the distal end 30 once the septum 60 and vacuum container 14 have been sufficiently withdrawn therefrom. Once completely removed, the device 10 of the present invention achieves the configuration depicted in FIG. 2. Having been used, the device 10 of the present invention may again be used as appropriate.

There has thus been provided a needleless vacuum container port system having the various embodiments and advantages set forth. It is to be understood, however, that modifications are possible within the spirit of the invention and that the claims should be interpreted as broadly as possible, and in light of the specification if need be.

What is claimed is:

1. An apparatus for depositing a sample of biological material into a vacuum container having a septum comprising:

(a) a bell-shaped housing having an open end for axially engaging with said septum of said vacuum container;

(b) at least one passageway disposed within said housing, said at least one passageway having a distal end through which said sample of biological material is passed into said vacuum container, said distal end of at least one passageway having means for penetrating said septum;

(c) a seal member affixed within said housing, said seal member axially sealing said distal end of said at least one passageway;

(d) wherein when said septum and said vacuum container are axially advanced into said opened end of said housing, said septum forces said seal member to axially retract about said distal end of said at least one passageway such that said distal end of said at least one passageway penetrates said septum of said vacuum container and allows said sample of biological material to be deposited within said vacuum container;

(e) wherein when said septum and said vacuum container are withdrawn from said opened end of said housing, said seal member axially advances about said distal end of said at least one passageway such that said passageway through which said sample of biological material is passed into said vacuum container is closed off;

(f) wherein said distal end of said at least one passageway comprises a hollow, spike-shaped member, said spike-shaped member being oriented toward said septum of said vacuum container; and (g) wherein seal member is fabricated from elastic material and is oriented such that said seal is biased toward said distal end of said at least one passageway such that said seal member continuously acts to close off said passageway through which said sample of biological material is deposited into said vacuum container.

* * * * *